United States Patent [19]
Gsell et al.

[11] Patent Number: 5,744,047
[45] Date of Patent: *Apr. 28, 1998

[54] LEUCOCYTE DEPLETING FILTER DEVICE AND METHOD OF USE

[75] Inventors: Thomas C. Gsell; Vlado I. Matkovich, both of Glen Clove; Thomas Bormann, Seaford, all of N.Y.

[73] Assignee: Pall Corporation, East Hills, N.Y.

[*] Notice: The term of this patent shall not extend beyond the expiration date of Pat. No. 5,362,406.

[21] Appl. No.: 294,051

[22] Filed: Aug. 24, 1994

Related U.S. Application Data

[63] Continuation of Ser. No. 221,983, Mar. 9, 1994, Pat. No. 5,362,406, which is a continuation of Ser. No. 827,488, Jan. 30, 1992, abandoned, which is a continuation of Ser. No. 558,468, Jul. 27, 1990, abandoned.

[51] Int. Cl.⁶ .......................... B01D 19/00; B01D 37/00; B01D 39/00; A61M 1/38
[52] U.S. Cl. .......................... 210/767; 210/436; 210/472; 210/493.1; 210/497.01; 210/503; 210/508; 210/805; 604/4
[58] Field of Search .................... 210/767, 788, 210/805, 188, 436, 472, 491, 493.1, 497.01, 497.1, 503, 508, 512.1; 55/521, 527; 96/209, 176; 604/4, 5, 6

[56] References Cited

U.S. PATENT DOCUMENTS

| | | | |
|---|---|---|---|
| 3,448,041 | 6/1969 | Swank | 210/496 |
| 3,593,854 | 7/1971 | Swank | 210/436 |
| 3,765,536 | 10/1973 | Rosenberg | 210/446 |
| 3,935,111 | 1/1976 | Bentley | 210/446 |
| 4,046,696 | 9/1977 | Mouwen | 210/431 |
| 4,092,246 | 5/1978 | Kummer | 210/767 |
| 4,115,277 | 9/1978 | Swank | 210/436 |
| 4,116,845 | 9/1978 | Swank | 210/436 |
| 4,246,107 | 1/1981 | Takenaka et al. | 210/806 |
| 4,283,289 | 8/1981 | Meyst et al. | 210/448 |
| 4,294,594 | 10/1981 | Sloane et al. | 210/436 |
| 4,330,410 | 5/1982 | Takenaka et al. | 210/767 |
| 4,416,777 | 11/1983 | Kuroda et al. | 210/508 |
| 4,572,724 | 2/1986 | Rosenberg et al. | 210/436 |
| 4,615,694 | 10/1986 | Raines | 604/406 |
| 4,662,906 | 5/1987 | Matkovich et al. | 210/436 |
| 4,701,267 | 10/1987 | Watanabe et al. | 210/505 |
| 4,726,901 | 2/1988 | Pall et al. | 210/496 |
| 4,828,543 | 5/1989 | Weiss et al. | 604/4 |
| 4,828,698 | 5/1989 | Jewell et al. | 210/266 |
| 4,880,548 | 11/1989 | Pall et al. | 210/767 |
| 4,923,620 | 5/1990 | Pall | 210/767 |
| 4,925,572 | 5/1990 | Pall | 210/767 |
| 4,936,998 | 6/1990 | Nishimura et al. | 210/767 |
| 4,964,984 | 10/1990 | Reeder et al. | 210/436 |

(List continued on next page.)

FOREIGN PATENT DOCUMENTS

| | | |
|---|---|---|
| 0155003 | 9/1985 | European Pat. Off. . |
| 0267286 | 5/1988 | European Pat. Off. . |
| 0315022 | 5/1989 | European Pat. Off. . |
| 0327136 | 8/1989 | European Pat. Off. . |
| 0370584 | 5/1990 | European Pat. Off. . |
| 2042919 | 10/1980 | United Kingdom . |
| 2056301 | 3/1981 | United Kingdom . |
| 2211755 | 7/1989 | United Kingdom . |
| 2216820 | 10/1989 | United Kingdom . |

OTHER PUBLICATIONS

Pall PL 100 Leukocyte Removal Filter, Pall et al. (Undated).
The Pall Blood Filter for Extracorporeal Service, Pall et al. (Undated).

(List continued on next page.)

*Primary Examiner*—John Kim
*Attorney, Agent, or Firm*—Leydig, Voit & Mayer, Ltd.

[57] ABSTRACT

Leucocyte depletion filter assemblies decrease the leucocyte content of a leucocyte-containing liquid at a flow rate of greater than about 25 milliliters per minute. These filter assemblies are suitable for use in an extracorporeal circuit. Methods for removing leucocytes and other deleterious matter are also disclosed.

35 Claims, 2 Drawing Sheets

U.S. PATENT DOCUMENTS

| | | | |
|---|---|---|---|
| 5,100,564 | 3/1992 | Pall et al. | 210/782 |
| 5,151,192 | 9/1992 | Matkovich et al. | 210/646 |
| 5,152,905 | 10/1992 | Pall et al. | 210/782 |
| 5,229,012 | 7/1993 | Pall et al. | 210/767 |
| 5,258,126 | 11/1993 | Pall et al. | 210/767 |
| 5,258,127 | 11/1993 | Gsell et al. | 210/767 |
| 5,266,219 | 11/1993 | Pall et al. | 210/767 |
| 5,316,674 | 5/1994 | Pall et al. | 210/257.1 |
| 5,362,406 | 11/1994 | Gsell et al. | 210/767 |

OTHER PUBLICATIONS

Intersept Extracorporeal Blood Filters, Johnson & Johnson Co. (Undated).

Bibliography of Swank Blood Filters for Extracorporeal Circulation, Swank et al. (Undated).

The Pall EC Plus Filter, Pall et al. (Undated).

AutoVent–SP, Pall et al. (Undated).

Pall RC 100 Leukocyte Removal Filter, Pall et al. (Undated).

Diepenhorst et al., "Removal of Leokocytes from Whole Blood And Erythrocyte Suspensions by Filtration through Cotton Wool", Vox Sanguinis, vol. 23, 1972, pp. 308–320.

Pall RC100™, Leukocyte Removal Filter For Blood Transfusion, Pall Corporation, ©1988, 8 pages (Brochure).

Bando, K. et al, "Leukocyte Depletion Ameliorates... Lung Injury After Cardiopulmonary Bypass", The Journal of Thoracic And Cardiovascular Surgery, vol. 99, No. 5, May 1990, pp. 873–877.

Finney, R.S. et al., "Polymorphonuclear Leukocyte Filtration In A Porcine Model of Cardiopulmonary Bypass", Current Surgery, vol. 46, No. 6, Nov./Dec. 1989, pp. 474–476.

Hall, T.S. et al., "The Role Of Leukocyte Depletion In Reducing Injury To The Lung After Hypothermic Ischemia", Current Surgery, vol. 44, No. 2, Mar./Apr. 1987, pp. 137–139.

Pillai, R. et al., "Leukocyte Depletion Results In Excellent Heart–Lung Function After 12 Hours Of Storage", The Annals of Thoracic Surgery, vol. 50, No. 2, Aug., 1990, pp. 211–214.

LEUCOCYTE DEPLETING FILTER DEVICE AND METHOD OF USE

This application is a continuation of application Ser. No. 08/221,983, filed Mar. 9, 1994, now U.S. Pat. No. 5,352,406, which is a continuation of Ser. No. 07/827,488, filed Jan. 30, 1992, abandoned, which is a continuation of Ser. No. 07/558,468, filed Jul. 27, 1990, abandoned.

TECHNICAL FIELD

The invention relates to filter devices for removing leucocytes and other deleterious material from leucocyte-containing liquids such as blood. For example, the invention relates to the removal of leucocytes from blood in an extracorporeal circuit.

BACKGROUND OF THE INVENTION

Patients undergoing open heart surgery have the pumping functions of the heart and the gas exchange functions of the lungs temporarily replaced by various apparatus in an external (extracorporeal) circuit. In the last 30 years, technological advances related to the components of these extracorporeal systems have provided significant benefits to these patients. For example, completely disposable components of an extracorporeal circuit and associated blood-contacting surfaces have been fabricated, which eliminate adverse patient reactions due to contamination from trace amounts of a previous patient's blood supply.

During a typical operation requiring extracorporeal circulation, blood from the cardiovascular system of the patient is typically taken from the patient and delivered through tubing to an oxygenator which serves as an external lung. Within the oxygenator, blood is exposed to an appropriate percentage of oxygen and carbon dioxide. The perfusate is drawn from the oxygenator by an arterial pump and delivered to a blood filter, which removes gaseous microemboli, fat emboli, aggregates and microaggregates, and other debris. From the filter, the blood is usually returned directly to the vascular system of the patient. Ancillary circuits, typically including one to three additional pumps and a small reservoir, may be used to salvage blood from the operative site. The salvaged blood is delivered to a cardiotomy reservoir where it can be filtered and stored until the surgeon returns the blood directly or indirectly through the oxygenator to the patient's cardiovascular system. By these means, the requirement for external blood replacement is often minimized.

The technological improvements noted above have focused on minimizing red cell damage in both the main circuit, comprising the oxygenator, arterial pump, and filter, and the ancillary blood salvage circuits. However, the presence of these devices, which are necessary for the transport and gas exchange of the blood but nonetheless are foreign to the patient's body, may have a deleterious effect on leucocytes, or white blood cells, in the blood. Contact between the internal surfaces of these foreign devices and the leucocytes may elicit an immune response and/or may result in the formation and release of a host of toxic mediators, and what is commonly referred to as oxygen-free radicals.

Leucocytes are a type of blood cell in the immune system which constitute the principal means of defense against antigens, such as infection by pathogenic microorganisms and viruses, and probably also against most cells that undergo transformation into cancer cells. Leucocyte activation, the leucocyte monitoring and arming functions, proceeds from a complex series of biochemical interactions, typically terminating in engulfing and digesting the antigen. If the leucocytes have been so activated, but lack an appropriate antigenic target, the leucocytes may inflict damage to internal organs, particularly ischemic tissues, i.e., tissues in which no blood is flowing such as the heart and lungs during certain surgical procedures. This effect, called "reperfusion injury", is well known and is commonly caused by leucocyte activation as a result of leucocyte contact with foreign matter such as the large internal surface area of an extracorporeal circuit.

The activated leucocytes associated with reperfusion injury release both proteolytic enzymes, which may lead to the destruction of cellular function and structure, and oxygen metabolites ("free radicals") which could lead to death. Extracorporeal circuit-induced activated leucocytes have been implicated in microcirculatory stasis, leucocyte sequestration, vasospasm, organ destruction, interstitial edema, microvascular occlusion (including myofibrillar necrosis, mitochondrial disruption, and nuclear chromatin clumping), lung endothelium damage, and the release of chemotactic factors.

Leucocytes have also been implicated as the singular cause or a major contributory factor in a growing number of transfusion complications, including non-hemolytic febrile reactions, alloimmunization, viral transmission (e.g., Cytomegalovirus, Human T-cell Lymphotropic Virus Type I), immune suppression and modulation, graft versus host reactivity, and refractoriness to platelets. Moreover, with increasing frequency, the most common leucocyte, the granulocytic neutrophil, has been implicated as the mediator of tissue destructive events in a variety of disorders, including reperfusion injury, respiratory distress syndrome, rheumatoid arthritis, skin disorders and ulcerative colitis. The commonality which pervades these pathologies is the neutrophil's ability to release a number of agents which can disrupt and destroy normal cellular function, dissolve connective tissue, and cause injury to organs.

It has also been shown that circulating leucocytes contribute to or mediate ischemic and reperfusion injury during organ preservation, particularly following extended preservation of the heart-lung bloc commonly required during cardiopulmonary bypass operations (CPB). Leucocytes have also been associated with increased oxygen radical activity, pulmonary edema, and vasoconstriction.

SUMMARY OF THE INVENTION

According to the present invention, a filter assembly for removing leucocytes and other deleterious matter from a liquid, such as blood, generally comprises a housing and a fibrous depth filter. The housing has an inlet and an outlet and defines a liquid flow path between the inlet and the outlet. The fibrous depth filter is positioned inside the housing across the liquid flow path and includes a fibrous structure for decreasing the leucocyte content of the liquid at a flow rate greater than about 25 milliliters per minute.

Filter assemblies which embody the invention may include a filter element having one or more of the following characteristics: a hollow, generally cylindrical configuration; an upstream portion which has a larger pore size than the downstream portion; a total fibrous surface area greater than about 2 square meters and a critical setting surface tension (CWST) of 53 dynes per centimeter or more. The filter assemblies may have a total hold-up volume in the range from about 70 cubic centimeters to about 400 cubic centimeters and may further comprise a porous degassing element for removing gas from the liquid, a liquophobic membrane which allows gas but not liquid to escape from the housing, and a vent for removing gas from the housing.

The present invention also provides a method for removing leucocytes and other deleterious matter from a liquid, such as blood. The method generally comprises decreasing the leucocyte content of the liquid by passing the liquid through a fibrous depth filter. Methods embodying the invention may include passing the liquid through a fibrous depth filter having one or more of the following characteristics: a hollow, generally cylindrical configuration; an upstream portion which has a larger pore size than the downstream portion; a total fibrous surface area greater than about 2 square meters; and a CWST of 53 dynes per centimeter or more. The method may further comprise holding up no less than about 70 cubic centimeters and no more than about 400 cubic centimeters of the liquid; repeatedly recirculating blood through a housing in an extracorporeal circuit; separating gas from the liquid; or venting the gas from the housing.

Filter assemblies and methods embodying the present invention are particularly advantageous. First, they remove leucocytes very effectively. Leucocytes are not only trapped in the interstices of the fibrous depth filter but they also adhere to the surfaces of the fibers in the depth filter. Having a total fibrous surface area greater than about 2 square meters, the fibrous depth filter provides ample surface area on which the leucocytes can adhere. Having a CWST of 53 dynes per centimeter or greater, the fibrous depth filter can have a CWST greater than the surface tension of the liquid, allowing the liquid to readily wet the fibrous depth filter, actively seep into all of the interstices of the filter element, and completely contact the ample surface area of the fibers.

Further, filter assemblies and methods embodying the present invention are capable of removing leucocytes while maintaining a large flow of liquid through the fibrous depth filter for a considerable span of time without clogging or plugging. Conventional filters may remove leucocytes at low flows, e.g., 5–10 milliliters per minute, but embodiments of the present invention are capable of removing leucocytes at much greater flow rates, even hundreds of times greater. As noted previously, because the CWST of the fibrous depth filter can be 53 dynes per centimeter or greater and, therefore, can be greater than the surface tension of the liquid, the liquid flows through the depth filter with minimal resistance due to the effects of surface tension. In addition, because the fibrous depth filter can have a hollow, cylindrical configuration and an upstream region with a larger pore size than the downstream region, the depth filter resists clogging or plugging. The hollow, cylindrical configuration presents a large surface area to liquid flowing outside-in through the depth filter and, therefore, spreads contaminants more thinly around the filter. The upstream region with the larger pores allows the smaller contaminants to penetrate deeper into the depth filter rather than accumulate on the surface of the filter to block liquid flow. Thus, although embodiments of the present invention are nonetheless effective at low flow rates, they are capable of removing leucocytes at very large flow rates for extended periods of time. For example, leucocytes may be removed from a liquid such as blood at a flow rate up to six liters per minutes for three to four hours and, in some cases up to ten hours, without clogging or plugging.

While filter assemblies and methods embodying the present invention are capable of maintaining a large flow rate, they hold up very little of the liquid when flow ceases. In many situations, the liquid being filtered is whole blood obtained directly from a patient. For example, during a surgical operation or during autologous transfusion, blood can be removed from the patient and circulated through an extracorporeal circuit which includes a filter assembly of the present invention, and then returned to the patient. When the operation is completed and flow through the extracorporeal circuit ceases, the blood which remains in the extracorporeal circuit, in particular, in the filter assembly, cannot be returned to the patient. Filter assemblies embodying the present invention hold up so little blood that only about 70 cubic centimeters to about 400 cubic centimeters remain in the filter assembly after flow ceases even though the flow rate during the operation can be as high as six liters per minute.

Filter assemblies and methods embodying the present invention have a wide variety of uses. For example, a filter assembly may be used to remove leucocytes and other deleterious matter from blood passing through it, while simultaneously allowing other blood components, such as red cells and platelets, to be returned undamaged to the patient.

A filter assembly or method embodying the present invention may be used in an extracorporeal circuit, such as is described above, and/or may be employed for therapeutic applications, including but not limited to autologous transfusion, leucopheresis, apheresis, or dialysis. Thus, the device and method have application whenever blood or a leucocyte-containing liquid is brought into contact with external circuitry, and thence returned to the body or specific organs.

A filter assembly or method embodying the present invention may also be used for cardioplegia or coronary perfusion in order to perfuse and maintain safe levels of metabolic activity within tissues and organs. Moreover, the filter assembly or method can be used for myocardial infarcted patients to reduce subsequent damage during reperfusion in the affected heart region.

In addition, a filter assembly in accordance with the present invention can be used in cytoreductive therapy or in any therapeutic or clinical regimen in which leucocyte depletion is beneficial. For example, certain hematological disorders result in a marked increase in blood viscosity due to a high number of circulating leucocytes. This phenomenon, called leukostasis, can result in tissue and organ damage. Extracorporeal circulation of blood through a device in accordance with the present invention can be used to reduce the leucocyte count, thus reducing blood viscosity.

Also, as noted above, leucocyte depletion has been successful in reducing or eliminating the deleterious effects attributed to a wide variety of injuries, diseases, or conditions. Passing the patient's blood through a device in accordance with the present invention can be used in clinical or therapeutic regimens in which leucocyte depletion is beneficial.

DESCRIPTION OF THE EMBODIMENTS

A filter assembly in accordance with the present invention comprises a housing, having an inlet and an outlet, and a filter element disposed in the housing for decreasing the leucocyte content and removing other deleterious matter from a leucocyte-containing liquid. Leucocyte-containing liquid, as used herein, refers to blood, including whole blood, treated blood, such as blood diluted with a physiological solution, and one or more blood components, such as plasma or packed red cells, as well as other leucocyte- or leucocyte precursor cell-containing liquids. Deleterious matter, as used herein, includes activated and non-activated leucocytes, fat emboli, microaggregates, and other debris. Preferred embodiments of the invention may also comprises a degassing mechanism cooperatively arranged with the housing for removing gaseous emboli from the liquid.

The filter assembly may be configured in a variety of ways in accordance with the invention. For example, the filter assembly may include a solid filter element which may have a disk-like or cylindrical shape and may be positioned in a housing to filter liquid flowing longitudinally or axially through the filter element. The inlet and outlet of the filter assembly would then communicate with opposite ends of the filter element and the side of the filter element would be sealed against the housing to prevent bypass of the liquid around the filter element.

Alternatively, the filter assembly may include a hollow filter elements which may have a cylindrical shape and may be disposed in the housing to filter liquid flowing laterally or radially through the filter element. For example, to filter liquid flowing inside/out through the filter element, the inlet and outlet of the filter assembly would be arranged to respectively communicate with the interior and exterior of the hollow filter element.

In the illustrated embodiment, the filter assembly is arranged to filter liquid flowing outside/in through the filter element. This arrangement is preferred because it provides a filter element with a large surface area in a compact housing.

The Housing

Figure 1:
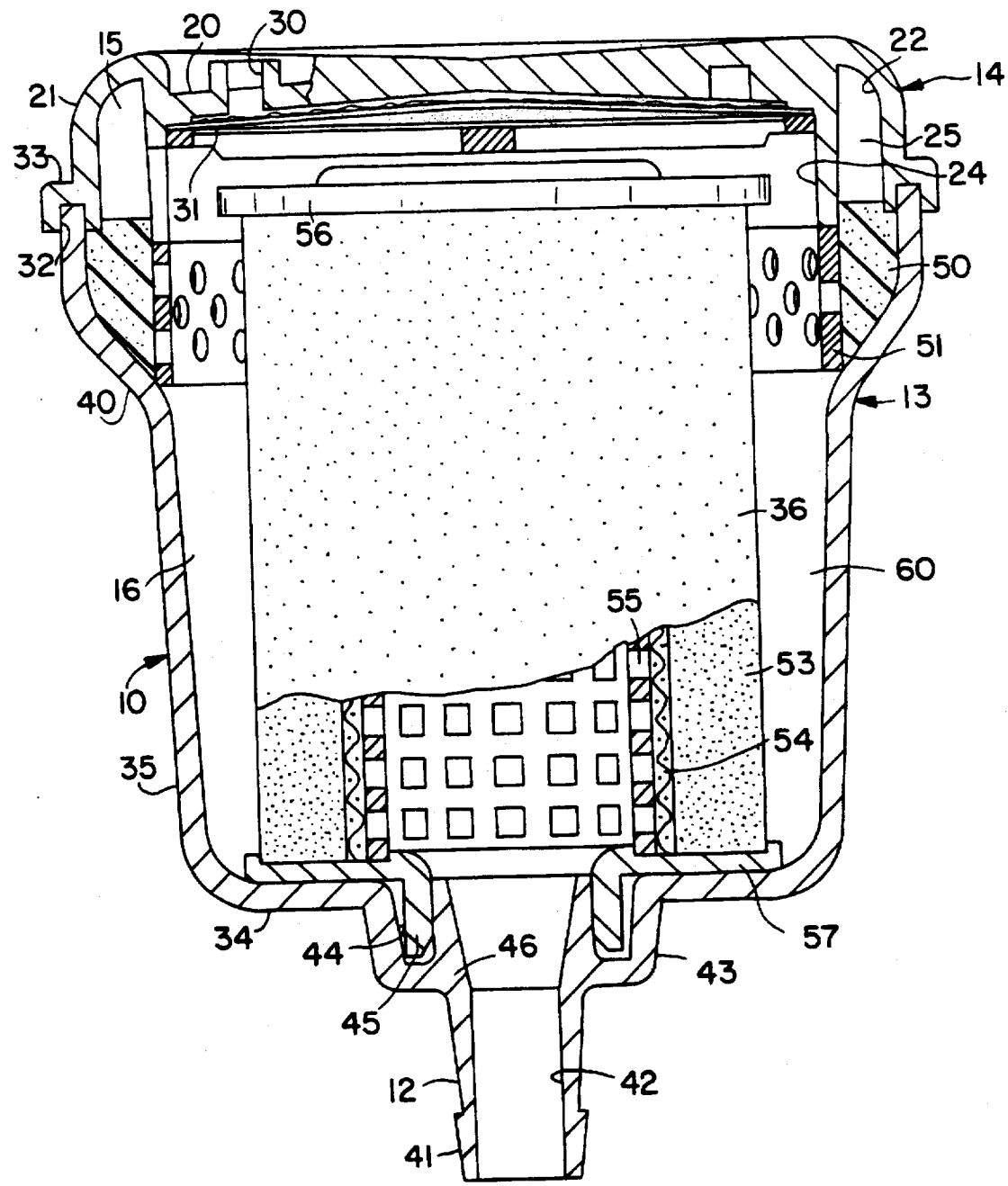
FIG. 1 is a sectional side view of an exemplary filtering apparatus embodying the present invention.
Figure 2:
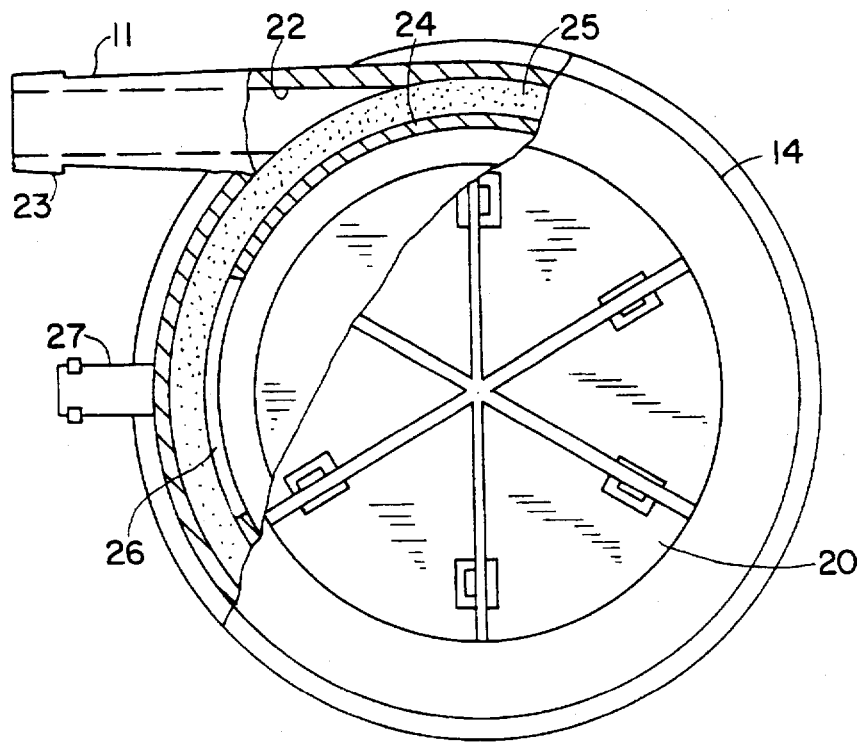
FIG. 2 is a partial cut away top view of the filtering apparatus of FIG. 1.

Any housing of suitable shape to provide an inlet and outlet for liquid and a space for a filter element disposed between the inlet and outlet can be employed. A preferred embodiment of the filter assembly comprises a generally cylindrical housing 10 having an inlet 11 and an outlet 12, as shown in FIGS. 1 and 2. Housings can be designed to accept a variety of shapes of filter assemblies. For example, a square or octagon shaped housing an other possible forms designed to accommodate a similarly shaped filter element would in principle all be functional, provided that adequate flow area is provided by the filter element. These shaped are within the scope of the claimed invention.

Any housing of suitable configuration to reliably contain the liquid and define a liquid flow path through the filter element can be employed. A preferred embodiment of the filter assembly comprises a housing 10 which generally includes two parts, a body 13 and a cover 14, and defines upper and lower chambers 15, 16. The cover 14 has a shallow, generally cylindrical configuration and includes a generally flat top wall 20 and a downturned, generally cylindrical, side wall 21.

In a preferred embodiment, the cover 14 includes the inlet 11, as shown in FIG. 2. The inlet 11 may be variously configured. For example, the inlet 11 may comprise a nipple 23 which defines an inlet passage 22 and may be molded integrally with the cover 14. In the illustrated embodiment, the inlet 11 is configured to receive the end of a tube (not shown). In a preferred embodiment, the inlet passage 22 is horizontal and opens through the side wall 21 of the cover 14 in a direction tangential to the side wall 21.

The cover 14 may also be provided with an accessory port 27 and an annular baffle 24. The accessory port 27 may be used to provide pressure measurements or samples of the liquid being filtered. When it is not in use, the accessory port 27 may be capped. The annular baffle 24 is preferably concentric with and spaced inwardly from the side wall 21. The baffle 24 may be formed integrally with the cover 14, extending downwardly from the top wall 20, and may be generally coextensive with the side wall 21, forming a circular channel portion 25 in the upper chamber 15. An opening 26 in the baffle 24 allows the circular channel 25 to communicate with a vent in the cover 14.

The vent allows gas to escape from the housing and may be configured in a variety of ways. For example, it may comprise a nipple with a manually operable valve. However, in a preferred embodiment, the vent comprises one or more holes 30 spaced around the top wall 20 of the cover 14. A porous, liquophobic membrane 31 may cover the holes 30 allowing gas but not liquid to escape from the housing. In a preferred embodiment, the liquophobic membrane may be attached to the underside of the top wall 20 of the cover 14 to allow a relatively free flow of gas from the housing. The liquophobic membrane may be variously configured. For example, it may comprise a polytetrafluoroethylene membrane, having an absolute pore rating of about 0.2 μ and a polypropylene backing as a support.

The cover 14 and the body 13 may be joined in any suitable manner. For example, the lower end of the cover side wall 21 may include an annular channel 32 formed in a flange 33 which is configured to receive the open upper end of the body 13. The cover 14 and the body 13 may then be joined at the channel 32, preferably by bonding or by welding, including spin welding or ultrasonic welding.

The body 13 includes bottom and side walls 34, 35 and may be substantially coextensive in depth with the height of the filter element 36. In a preferred embodiment the side wall 35 of the body 13 generally has a smaller outer diameter than the side wall 21 of the cover 14 but flares at the upper end to provide an inclined shoulder 40.

In a preferred embodiment, the body 13 includes the outlet 12. The outlet 12 may be variously configured. For example, the outlet 12 may comprise a nipple 41 which defines an outlet passage 42 and may be molded integrally with the body 13. In the illustrated embodiment, the nipple 41 projects axially down form a boss 43 in the center on the underside of the bottom wall 34 and is configured to receive the end of a tube (not shown). An annular groove 44 in the inside of the boss receives an annular extension 45 which surrounds an extension 46 of the nipple 41 and which centrally locates the filter element 36 in the body 13.

The housing may be fabricated from any sufficiently rigid, impervious material which is compatible with the leucocyte-containing liquid. For example, the housing may be fabricated from a metal, such as stainless steel, or from a polymer. In a preferred embodiment, the housing is fabricated from a plastic material, such as polystyrene, polycarbonate, or polypropylene. In addition, all of the surfaces of the housing which contact the liquid are preferably liquophilic, i.e., readily wettable by the liquid. For example, the internal surfaces of the body 13 and the cover 14 may be treated to achieve a high degree of liquophilicity, e.g., by surface graft co-polymerization of hydroxyl functional monomers. These liquophilic internal surfaces than readily facilitate the release of gas bubbles during the prep and priming operation. A method of reducing the adhesion of bubbles in medical equipment is disclosed in U.S. Pat. No. 4,861,617.

The Degassing Element

The degassing element may be fashioned from any material which causes small gas bubbles in the liquid to coalesce and separate from the liquid. In a preferred embodiment, the degassing element is a porous structure such as a porous foam or sponge material. In addition, the degassing element may be treated with an anti-foaming agent to aid in breaking down the film between bubbles, for example, a compound of silicone and silica, such as Medical Antifoam A, available from Dow Corning Mfg. Co.

The degassing element may have any suitable configuration, preferably geometrically similar to the shape of the housing, and is preferably positioned in the housing between the inlet and the filter element. For example, in the illustrated embodiment, the degassing element comprises an annular sponge 50 interposed between the upper and lower chambers 15, 16. The annular sponge 50 may be located in the housing 10 by an annular, perforated ring 51 which preferably constitutes, in effect, an axial extension of the baffle 24. The inclined shoulder 40 holds the annular sponge 50 and perforated ring 51 in place in the flared portion of the housing body 13.

The illustrated embodiment of the filter assembly includes a degassing element 50 as well as a housing 10 having a tangential inlet 11 and a vent 30, all for removing gas from the liquid before the liquid contacts the filter element 36. Of course, the gas may be removed from the liquid by a separate device before the liquid enters the filter assembly. The filter assembly then need not include a degassing element, a tangential inlet, or a vent. The housing may then simply be only slightly larger than the filter element.

Filter Element

In accordance with one aspect of the invention, the filter element may be fashioned to decrease the leucocyte content of a leucocyte-containing liquid which is passed through the filter element. The filter element may be fashioned in a variety of ways to effectively remove the leucocytes, as well as other deleterious matter from the liquid. For example, the filter element preferably comprises a depth filter. The depth filter may preferably comprise a mass of fibers, such as a mass of microfibers. The fibers may be made from any material compatible with the liquid and may be untreated or may be treated in a variety of ways to make the filter element even more effective. The fibers may be bonded, fused, or otherwise fixed to one another or they may simply be mechanically entwined.

The fiber diameters and/or the void space between the fibers may have a substantially constant size along the dimensions of the filter element or they may vary in a continuous or stepwise manner. Further, the filter element may be configured as a flat sheet, a corrugated sheet, a solid body such as a disk or cylinder, or a hollow body such as a hollow cylinder and may include additional structures such as end caps, edge seals, a cage, a core, or a wrap.

As shown in FIG. 1, a preferred embodiment of the filter element 36 has a hollow, generally cylindrical configuration and comprises a wrap (not shown), a fibrous mass 53, a porous element 54, a perforated core 55, an upper blind end cap 56, and a lower open end cap 57. The filter element 36 is preferably disposed within the lower chamber 16 in the housing 10 and is smaller in diameter than the side wall 15 of the body 13 so that an annular space 60 is left between the side wall 35 and the filter element 36. The interior of the filter element 36 communicates with the centrally located outlet 12.

The wrap surrounds the fibrous mass 53 and serves to protect the fibrous mass 53 from damage when the filter element 36 is assembled. The wrap may comprise any sufficiently flexible, porous material, preferably having a relatively large pore size. For example, the wrap may be a sheet of spun-bonded, non-woven, polypropylene fibers.

The porous element 54, which preferably has a pore size no greater than about 40 microns, is disposed coaxially adjacent to the downstream surface of the fibrous mass 53, e.g., around the interior of the fibrous mass 53. The porous element 54 may be fashioned from any compatible porous membrane or woven or non-woven material, including a mesh or a screen. The porous element 54 serves principally as a final filter to remove, for example, any aggregates which escape the fibrous mass 53 or form at the downstream portion of the fibrous mass 53.

The perforated core 55 is disposed within and adjacent to the interior of the porous element 54 and serves principally to support the fibrous mass 53 and the porous element 54 against the differential pressure across the filter element 36. Consequently, the perforated core 55 may be fashioned from any suitably rigid material including a metal such as stainless steel or a rigid polymer such as polyolefin, polyester, or polyacrylate.

The end caps 56, 57 serve to direct the liquid radially outside/in through the filter element 36. Both end caps 56, 57 are preferably fashioned from an impervious polymer, such as polypropylene, and are fixed to the respective ends of the fibrous mass 53, the porous element 54, and the perforated core 55. Alternatively, the lower ends of the fibrous mass, the porous element, and the perforated core may be fixed directly to the bottom wall of the body, eliminating the need for a lower end cap.

Alternatively, the filter element may be designed for inside/out flow. The porous element may then be disposed around the exterior of the fibrous mass, the upper end cap may be an open end cap, and the lower end cap may be a blind end cap. The core may be omitted but a cage disposed coaxially around the porous element to support the fibrous mass and the porous element against the pressure drop may be added. Of course, the housing would be rearranged to permit the inlet to communicate with the interior of the filter element and the outlet to communicate with the exterior of the filter element.

Fibrous Mass

The fibrous mass 53 may preferably be configured as a mass of non-woven, synthetic, polymeric fibers. The fibers may be bonded, fused, or otherwise fixed to one another, or they may be substantially free of fiber-to-fiber bonding and secured to each other by mechanical entanglement or intertwining. The term "fibers" includes filaments, and the term "substantially free of fiber-to-fiber bonding", as used herein, refers to the characteristics of the fibers making up the fibrous mass 53. Thus, although the fibrous mass 53 may display random fiber-to-fiber bonding, such bonding would not contribute in any material way to the structural integrity of the filter element. A preferred fibrous mass 53 is available from Pall Corporation under the registered trademark Profile.

Polymeric materials particularly well suited for the fibrous mass 53 include, but are not limited to thermoplastics such as the polyolefins, particularly polypropylene and polymethylpentene; polyamides, particularly nylon 6, nylon 610, nylon 10, nylon 11, nylon 12; and polyesters, particularly polybutylene terephthalate and polyethylene terephthalate. Other suitable, but less preferred, polymers are addition polymers such as polyvinyl fluoride, polyvinylidene fluoride and their copolymers. The preferred material is polybutylene terephthalate.

The fibrous mass 53 may be produced by melt blowing, in which molten resin is attenuated into fibers by a high velocity stream of gas and collected as a non-woven web. As disclosed in U.S. Pat. No. 4,726,901, of the above noted materials, some are better adapted to melt blowing of fine fibers than are others. Material which are particularly suited to melt blowing include polyethylene, polypropylene, polymethylpentane, Nylon 6, polyester PET (polyethylene terephthalate), and polyester PBT (polybutylene terephthalate). Others that have not yet been tested may be found. Of the above listed resins, polyester PBT is a preferred material because it also lends itself a radiation grafting.

For some applications it may be desirable to form the fibrous mass 53 directly on a mandrel without the use of an internal support or core. For most purposes, however, it is desirable that the structure be able to withstand, without collapse or loss of integrity, differential pressures in the range from about 0.5 psid to about 175 psid, preferably in the range from about 0.5 psid to about 135 psid. Accordingly, for most applications, it is desirable to form the fibrous mass 53, preferably by depositing melt-blown fibers, on a hollow foraminous, or open, relatively rigid central support member or core 55 after the porous element 54 has been mounted to the core 55.

The fiber diameters may be substantially constant throughout the fibrous mass 53. Alternatively, the fiber diameters can be varied in a continuous or step-wise manner from one part of the fibrous mass 53 to another as measured in the radial direction by varying the resin and fiberizing air flow rates. Without intending to be held to a specific theory, a combination of adsorption and mechanical entrapment of leucocytes on fiber surfaces is believed to be the mechanism for removing the leucocytes from a leucocyte-containing liquid. Since the surface area of a given weight of fibers is inversely related to the diameter of the fibers, it is to be expected that finer fibers will have higher capacity and that the quantity of fibers, as measured by weight of fibers necessary to achieve a desired efficiency, will be less if the fibers used are smaller in diameter. Fiber diameters as small as about 1.5 to about 2 micrometers or less may be used to fashion the fibrous mass 53.

The fibrous mass 53 also preferably has a substantially constant voids volume, typically in the range of from about 60 to about 95 percent, more preferably from about 64 to about 93 percent and even more preferably from about 75 to about 85 percent. When the fibrous mass 53 comprises polybutylene terephthalate (PBT) fibers, the most preferred voids volume is about 85 percent. The voids volume can be maintained substantially constant by varying the forming roll bias force on the cylindrical mass of fibers 53 as the structure is formed on the rotating porous element 54 and core 55.

The removal rating can vary with the fiber diameter. Thus, by varying the fiber diameter, removal rating can be varied continuously or stepwise from one part of the fibrous mass 53 to another in any desired manner in order to form a filter element 36 having a graded pore structure. For example, the fibrous mass 53 may include an upstream portion having a removal rating as large as about 120 micrometers and a downstream portion having a removal rating as small as about 0.5 micrometers, each at a beta equal to 5000. More preferably, the upstream portion may have a removal rating as large as about 70 micrometers and the downstream portion may have a removal rating as small as about 5 micrometers, each at a beta equal to 5000. Such a fibrous mass may be embodied with an upstream portion having coarser fibers than the downstream portion.

In the illustrated embodiment, the annular thickness of the fibrous mass 53 is preferably in the range from about 0.1 to about 2 inches (2.5 mm to 5 cm), more preferably in the range from about 0.4 to about 0.8 inch (1.0 to 2.0 cm), and most preferably in the range from about 0.6 to about 0.7 inch (1.5 to 1.8 cm). The outer diameter of the fibrous mass is preferably in the range from about 2 to about 3 inches (5 to 7.5 cm), more preferably about 2.2 (5.5 cm) inches. The length of the fibrous mass 53 is preferably in the range from about 2 to about 3 inches (5 to 7.5 cm), more preferably about 2.5 inches (6.4 cm).

Surface Modification of Fibers

Although the fibers of the microfibrous mass 53 may remain untreated, they are preferably treated to make them even more effective for removing leucocytes and other deleterious matter. For example, the fibers may be surface modified to increase the critical wetting surface tension (CWST) of the fibers.

As disclosed in U.S. Pat. No. 4,880,548, the CWST of a porous medium may be determined by individually applying to its surface a series of liquids with surface tensions varying by 2 to 4 dynes/cm and observing the absorption or non-absorption of each liquid over time. The CWST of a porous medium, in units of dynes/cm, is defined as the mean value of the surface tension of the liquid which is absorbed and that of the liquid of neighboring surface tension which is not absorbed within a predetermined amount of time. The absorbed and non-absorbed values depend principally on the surface characteristics of the material from which the porous medium is made and secondarily on the pore size characteristics of the porous medium.

Liquids with surface tensions lower than the CWST of a porous medium will spontaneously wet the medium on contact and, if the medium has through holes, will flow through it readily. Liquids with surface tensions higher than the CWST of the porous medium may not flow at all at low differential pressures and may do so unevenly at sufficiently high differential pressures to force the liquid through the porous medium. In order to achieve adequate priming of a fibrous medium with a leucocyte-containing liquid such as blood, the fibrous medium preferably has a CWST in the range of about 53 dynes/cm or higher. A CWST in the range from less than 53 dynes/cm to 115 dynes/cm or greater is preferred. For example, a CWST of greater than about 90 dynes/cm is expected to provide better passage and protection of the platelets as they pass through the porous medium. Methods for increasing the CWST in the range of 53 or greater are disclosed in U.S. Pat. No. 4,925,572. Methods for increasing the CWST in the range of 90 or greater are disclosed in U.S. Pat. No. 4,880,548.

For example, in whole blood, the cellular components are suspended in blood plasma, which typically has a surface tension of 73 dynes/cm. Hence, if whole blood is placed in contact with the microfibrous mass 53, spontaneous wetting will occur if the microfibrous mass 53 has a CWST of about 73 dynes/cm or higher.

The benefits conferred by modifying fibers to CWST values higher than the natural CWST of synthetic fibers include:

(a) When priming using pressures lower than the 0.2 kg/cm², for example by gravity, the time to achieve priming is significantly reduced. At 0.2 kg/cm², the reduction is, however, so small as to be difficult to measure.

(b) Fibrous media treated to convert the fiber surfaces to a particular range of CWST perform better with respect to efficiency and resistance to clogging than do fibrous media with CWST values outside of those ranges.

(c) The detrimental effects associated with non-wetting, e.g., uneven flow through the porous medium, are avoided.

(d) Devices made using unmodified synthetic fibers are recommended to be flushed with saline prior to use. This operation is sometimes undesirable since it causes blood loss due to hold-up within the complex tubing arrangement required, adds to cost, operation time, and operation complexity, and increases and probability that sterility may be lost.

Surface characteristics of a fiber can be modified by a number of methods, for example, by chemical reaction including wet or dry oxidation, by coating the surface by depositing a polymer thereon, and by grafting reactions which are activated by exposure to an energy source such as heat, a Van der Graff generator, ultraviolet light, or to various other forms of radiation. The preferred method is a grafting reaction using gamma-radiation, for example, from a cobalt source.

Radiation grafting, when carried out under appropriate conditions, has the advantage of considerable flexibility in the choice of reactants, surfaces, and in the methods for activating the required reaction. Gamma-radiation grafting is particularly preferable because the products are very stable and have undetectably low aqueous extractable levels. Furthermore, the ability to prepare synthetic organic fibrous media having a CWST within a desired range is more readily accomplished using a gamma radiation grafting technique.

An exemplary radiation grafting technique employs one or more of a variety of monomers each comprising an ethylene or acrylic moiety and a second group, which can be selected from hydrophilic groups (e.g., —COOH, or —OH) or hydrophobic groups (e.g., a methyl group or saturated chains such as —CH₂CH₂CH₃). Grafting of the microfibrous mass 53 may also be accomplished by compounds containing an ethylenically unsaturated group, such as an acrylic moiety, combined with a hydroxyl group, such as, hydroxyethyl methacrylate (HEMA). Use of HEMA as the monomer contributes to a very high CWST. Analogues with similar characteristics may also be used to modify the surface characteristics of fibers.

Radiation grafting may increase fiber-to-fiber bonding in a fibrous medium. Consequently, a fibrous medium which exhibits little or no fiber-to-fiber bonding in an untreated state may exhibit significant fiber-to-fiber bonding after the fibers have been radiation grafted to increase the CWST of the medium.

Mode of Operation

In a preferred embodiment of the invention, a leucocyte-containing liquid enters a filter assembly of the present invention through inlet passage 22 and into the circular channel 25 in upper chamber 15 where a generally circular liquid flow pattern is maintained by annular baffle 24 and the side wall 21 of the cover 14. This flow pattern produces a centrifugal force which causes at least some of the gas bubbles in the liquid, including any gross gas bubbles, to separate from the liquid and move inwardly and through the opening 26 in the baffle 24 into the central portion of the upper chamber 15. The gas in the liquid is then vented from the filter assembly through the holes 30 in the cover 14. In a preferred embodiment of the invention, the gas passes through a liquophobic membrane 31, which covers the holes 30 and prevents the liquid from escaping from the housing 10.

The liquid in channel 25 then passes, in a preferred embodiment, through the annular sponge 50 and the perforated ring 51 to the space 60 in the lower chamber. The degassing element 50 brakes the rotational flow of the liquid and dissipates the centrifugal forces which might otherwise tend to force gas bubbles toward the filter element 36. Also, as the liquid passes through the degassing element 50, any smaller gas bubbles remaining in the liquid coalesce into larger bubbles which, as the liquid flows through the perforations in the perforated ring 51, rise to the central portion of the upper chamber 15 and are vented from the filter assembly as noted above. Thus, the liquid which flows into the space 60 is substantially degassed.

In the embodiment of the invention characterized as "outside/in," the degassed liquid then passes from space 60 through filter element 36, and into the interior of the filter element 36. The filtered liquid then flows from the interior of the filter element and exits from the housing 10 by passing through outlet 12.

In a preferred embodiment, the filter element 36 comprises a fibrous mass 53 having a graded pore size, e.g., one wherein the removal rating varies continuously or step-wise from a relatively large size in the upstream portion of the fibrous mass to a relatively small size in the downstream portion. It is believed that filter element 36 decreases the leucocyte content of the liquid by two mechanisms, both operating simultaneously. One mechanism is by adsorption of the leucocytes and other deleterious matter onto the fibrous surfaces. Adsorption is a function of the surface area of the fiber, which may be in turn a function of fiber diameter; adsorption may also be affected by the CWST of the fiber. The surface area required for specific uses of the filter assembly will vary according to the use. For example, in an extracorporeal circuit with a flow rate of as much as six liters/minute, the fiber surface area of the filter element is preferably in excess of about two or three square meters. However, for some applications, it will be desirable to have a smaller quantity of fiber and/or fiber surface are incorporated into a significantly smaller filter assembly. An example is the "low flow" embodiment described below. Generally, the surface are of the fibers is sufficient to permit a large number of contacts between individual fibers of the fibrous mass and leucocytes and deleterious matter in the liquid.

The second possible mechanism, removal of filtration or mechanical entrapment, depends principally upon maintaining the removal rating of the filter medium within a specific range, but may be marginally affected by the fiber CWST. In a preferred embodiment, the removal rating is preferably between about 5 micrometers and about 70 micrometers. The smaller the fiber diameter, the higher the surface area (per gram) and the smaller the effective pore size.

The flow rate of liquid passing through a filter assembly of the present invention can vary according to the particular use and for any given patient, but the flow rate should be maintained at a level which does not harm or destroy erythrocytes or platelets in the liquid. Embodiments of the invention may filter as little as 25 milliliters per minutes or may have the capacity to filter up to about 6 liters of liquid per minute, preferably about 4 to about 6 liters per minute, without clogging (i.e., without increasing the pressure across the filter element to above about 15 psi). It should be apparent to one skilled in the art that varying the surface area, CWST, flow rate, removal rating, fiber diameter, and size of the housing may affect leucocyte removal capacity. Individually optimizing each of these parameters for a specific intended use is considered within the scope of the present invention.

The size of the filter assembly housing, the surface area of the fiber, the pore diameter, and the CWST all may affect the hold-up volume and the priming efficiency of the filter assembly. Hold-up volume refers to the amount of fluid required to obtain filtered fluid at the output end of the filter assembly. Hold-up volume also refers to the amount of fluid which remains in the filter assembly after it is taken off-line. Preferably, the hold up volume is between about 70 cc and about 400 cc, typically between about 180 cc to about 250 cc. One skilled in the art will recognize that changing the design characteristics of the filter assembly may affect the hold-up volume. For example, increasing the size of the filter housing may increase the hold-up volume and removing the degassing element may decrease the hold-up volume.

Priming efficiency refers to start-up of flow from the patient through the filter and back to the patient. An advantage of the filter assembly embodying this invention is that the priming time may be below about 2 minutes. A short priming period may be desirable in order to conserve nurse/technician time, but may also be a life-saving issue when quick administration is required as, for example, when serious blood loss is unexpectedly experienced during surgery.

While the devices described herein are principally directed to a filter assembly having a capacity of passing up to about 6 liters/minute, filter assemblies having a larger or smaller capacity can be made. Included within the scope of the invention is a filter assembly designated as a "low flow" size, which has a flow rate of about 3 liters/minute or less, has approximately one-third the fiber surface area and about one-half the capacity of the adult device.

A filter assembly according to the present invention has the capacity for up to about 10 hours of continuous removal of a clinically or therapeutically significant amount of leucocytes and other deleterious matter from a leucocyte-containing liquid. However, many of the uses for which these filter assemblies are suitable do not require 10 hours of filtration. For example, a cardiac bypass operation may only require 6–8 hours; cardioplegia may require only 2–4 minutes of filtration. Some therapeutic protocols performed under emergency conditions require only 10–20 seconds of filtration, or several periodic or repeated filtrations of about 10–20 seconds duration.

A filter assembly in accordance with the present invention is capable of decreasing the leucocyte content of the leucocyte-containing liquid. This generally means removing a therapeutically or clinically significant amount of leucocytes from a leucocyte-containing liquid. "Therapeutically or clinically significant amount" refers an amount necessary to produce a beneficial effect on the patient or animal receiving the leucocyte depleted liquid. Such a beneficial effect may be, for example, lessening reperfusion injury. A therapeutically or clinically significant amount can vary depending on the intended use and/or from patient to patient. For example, a therapeutically or clinically significant amount can be greater for a cardiac bypass procedure than for cardioplegia. However, removal of a therapeutically or clinically significant amount can be and is routinely determined by a doctor or technician for treating a certain condition or disease as it pertains to the specific patient or animal, and as it pertains to the particular application.

For example, in an extracorporeal circuit, a reference point (control) leucocyte count is obtained immediately prior to the operation. Once the operation begins, however, the patient is constantly producing new leucocytes. Additionally, the number of circulating leucocytes can be increased merely through the doctor's alteration of an operative condition, e.g., adding Hespan to the circulating blood or increasing the pump speed. Furthermore, what is normal for one patient may be abnormal for another. However, when an embodiment of the invention is used in an extracorporeal circuit, the leucocyte content is decreased, resulting in a therapeutically or clinically significant removal of leucocytes and demonstrably less reperfusion injury. Also, an embodiment of the invention may be used in an extracorporeal circuit whereby the leucocyte content in the circulating blood achieves equilibrium, i.e., the amount of leucocytes produced by the patient is substantially offset by the removal of leucocytes using a leucocyte depletion filter assembly according to the present invention.

Furthermore, achieving leucocyte depletion in and of itself, in relation to the initial leucocyte count, may also be therapeutically or clinically significant. Some therapies require the removal of a certain number of leucocytes, e.g., to quickly reduce a high leucocyte count to a lower one. Under these conditions, the mere reduction in leucocyte count may be therapeutically significant.

A filter assembly of the present invention may be used in any procedure, therapy, operation, or environment in which the removal of activated leucocytes and deleterious matter is desirable or beneficial. Because leucocytes have the potential for becoming activated upon contact with almost anything ex-vivo, many applications exist for the use of the filter assemblies of the present invention in reducing the number of activated leucocytes. While the filter assembly of the present invention is particularly suited for treating reperfusion-induced injury and/or achieving leucocyte content equilibrium in an extracorporeal system, one skilled in the art will recognize other contexts in which removal of leucocytes and other deleterious matter in a liquid is desirable. Without intending to limit the invention thereby, the following provides examples of such uses.

A filter assembly of the present invention may be used in any procedure which requires perfusion, the passage of blood or other fluid through the blood or lymph vessels of the body, using blood or other fluid which has been exposed to anything ex-vivo (and therefore potentially containing activated leucocytes). For example, a filter assembly according to the present invention may be used in any of the different techniques for protecting the heart during ischemia (no flood flow) to the heart. This is particularly evident in cardiac bypass operations, including but not limited to left heart bypass, femoral-femoral bypass, and aortic occlusion. Also, leucocyte depletion has been implicated in the amelioration of a number of diseases or conditions, including the reduction of pulmonary injury seen after CPB. Leucocyte depletion appears to be the source of excellent cardiac and pulmonary protection.

Figure 3:
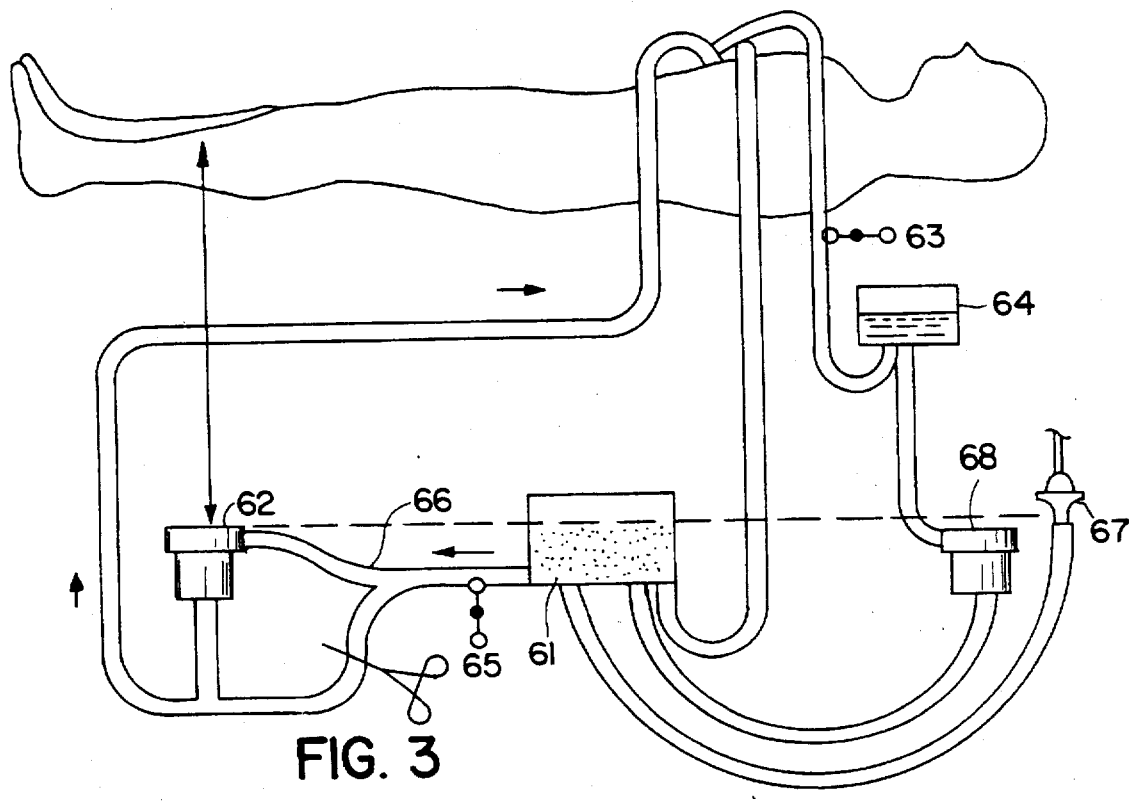
FIG. 3 is an illustration of a liquid filtering system incorporating the filtering apparatus of FIG. 1.

Without intending to limit the invention thereby, an exemplary mode of operation for an embodiment of the invention is described by reference to an extracorporeal (EC) system used in a cardiopulmonary bypass (CPB) operation, as illustrated in FIG. 3, which shows the use of the same filter under different capacity requirements.

In a CPB operation, the EC system commonly comprises two loops. The first loop is a CPB circuit for bypassing the patient's heart and lungs, i.e., involved in rendering the heart ischemic. The second loop is a cardiotomy circuit for collecting blood from the operative site.

The EC system is primed by clamping the inlet and outlet tubing of filter assembly 62. The rest of the circuit is then primed using the bypass circuit 66 by passing a priming fluid, such as physiological saline, through the circuit at a flow rate of about 3–6 liters per minute. While maintaining this flow, the clamp near the outlet of the filter assembly is partially opened, allowing the filter assembly to slowly fill with perfusate. The filling time is preferably no more than about 2 minutes. When the priming fluid reaches the top of the filter, the outlet clamp is removed, then the inlet clamp is removed, and finally, the bypass circuit is clamped.

Once the system is primed, blood from the cardiovascular system of the patient is channeled into the CPB circuit through tubing into an oxygenator 61 which removes carbon dioxide from the blood and replaces it with oxygen. Oxygen is delivered to the oxygenator 61 through an oxygen filter 67. A pump 65 draws the oxygenated blood through a filter assembly 62 of the present invention, after which the filtered blood is returned to the cardiovascular system of the patient.

In the cardiotomy circuit, excess blood from the surgical site is removed from the patient by pump 63 and delivered to a cardiotomy reservoir 64. Periodically, blood is drawn (or flows by gravity) from the cardiotomy reservoir 64 into a filter assembly 68 of the present invention, and then into the oxygenator 61, where it is mixed with the blood in the CPB circuit. Filter assemblies 62 and 68 may be the same type of filter assembly, or they may be different, but both are intended to be a filter assembly according to the present invention. Thus, a filter assembly of the present invention may be used in environments which require a capacity of up to 6 liters/minute, and which function at that level (for example, the CPB circuit) or at a fraction of that level (for example, the cardiotomy circuit).

In addition to the extracorporeal circuit described above, another use of the filter assemblies of the present invention include arterial line filters, wherein the blood which flows through the circuit comes from a patient's artery. Typically, the pressure needed to produce throughflow is the patient's blood pressure, but it may be supplemented by an in-line pump. Similar to the extracorporeal circuit noted above, arterial line filters according to the invention have the capacity to achieve leucocyte equilibrium. In use, establishing leucocyte equilibrium indicates that the leucocyte count when the filter assembly is present is lower than the leucocyte count when the filter assembly is not present.

More and more, cardiopulmonary bypass, as a treatment or surgical protocol, is being extended to non-cardiac applications as the knowledge concerning the pathogenic nature of leucocytes increases. All of these protocols may be improved by the inclusion of a leucocyte depletion filter of the present invention. For example, neurosurgeons use CPB in operations involving the brain, the central nervous system, and for the surgical repair of aneurysms, fistulae, cerebral blood vessel anomalies, and blood clots. CPB is also used in abdominal surgery to provide a means of hypothermia and circulatory arrest, and for isolating the abdominal venous circulation. CPB may also be used in exposure hypothermia to rewarm the victim and to offset or eliminate myocardial damage. CPB is used for whole body hyperthermia in the treatment of certain cancers which are sensitive to elevated temperatures. CPB may be used in isolated limb perfusion in order to eliminate or reduce the transport of toxic drugs and their side effects by compartmentalizing blood flow. An embodiment of the invention may be incorporated into any of these protocols in order to achieve a clinically or therapeutically significant effect.

Leucocyte depletion using a filter assembly of the present invention may also ameliorate common post-hypothermia pathologies.

In organ transplantation, the success of the transplant may depend on suppressing the body's natural tendency to rid itself of "foreign" tissue. This can be achieved through a variety of powerful immunosuppressive drugs, some of which kill lymphocytes, and others of which stimulate antibodies that inactivate lymphocytes. Included within the scope of this invention are therapies which combine the use of immunosuppressive drugs and filtering circulating blood to remove deleterious material from the bloodstream. In liver transplantation, massive blood loss and blood usage, as well as reducing or eliminating donor organ damage due to activated leucocytes, would benefit from leucocyte depletion using a filter assembly of the present invention.

Also included within the scope of this invention is the use of a filter assembly in procedures with ischemic or ischemic-like episodes, and for the reperfusion of blood for the whole body, for regional areas, or for isolated areas.

Leucocyte depletion, and the filter assemblies of the present invention, may also be used therapeutically for conditions in which leucocytes play an interactive role with vascular endothelial cells, including but not limited to Adult Respiratory Distress Syndrome, allograft rejection, shock states, coronary occlusion, and stroke.

The filter assembly of the present invention is also particularly useful in therapeutic protocols involving spheresis, either alone, or in conjunction with other therapies. Leucopheresis, the selective removal of leucocytes, may be used to obtain leucocyte donation or as a therapeutic measure in patients with elevated peripheral blood white cell count. A wide number of disorders, diseases and conditions may be diagnosed and/or treated using leucopheresis. The filter assemblies of the present invention may be used as or in a leucopheresis apparatus.

A filter assembly of the present invention may also be used in a wide variety of therapies for treating autoimmune diseases (e.g., systemic lupus erythematosus, rheumatoid arthritis, thyroiditis, myasthenia gravis, multiple sclerosis, and certain kinds or anemia). These therapies include radiation of the lymph nodes, immunosuppressive drugs developed as anti-cancer agents, and spheresis, a sort of "blood washing" that removes diseased cells and harmful molecules from the circulation. For example, special leucocytes (e.g., labeled and/or killer leucocytes) have been and are being developed for the diagnosis and treatment of disorders involving neoplastic cells. A filter assembly of the present invention may be used to remove these special leucocytes after they have performed their therapeutic or diagnostic function.

A filter assembly of the present invention may also be used in the treatment of viral infections and diseases. In the blood, viruses may be present in the plasma, or may be associated with particular types of leucocytes, with platelets, or with erythrocytes. Leucocyte-associated viremia (the presence of a virus in the bloodstream) is a feature of several types of infection, including but not limited to infectious mononucleosis, measles, and smallpox. Circulating leucocytes are themselves a source of replicating virus; viremia is usually maintained if there is a continued release of the virus into the blood. For example, post-transfusion mononucleosis (also known as postperfusion syndrome) is a febrile condition commonly seen in patients receiving massive blood transfusion (e.g., for open-heart surgery). Cytomegalovirus (CMV) can be isolated from the leucocytes of these patients. Latent CMV infection also commonly occurs in patients undergoing prolonged immunosuppressive therapy for kidney transplants, leukemia, or cancer. In addition, infectious mononucleosis is also associated with Epstein-Barr Virus (EBV), typically manifested by leucopenia followed by leucocytosis. Treatment of these conditions may be facilitated by using a filter assembly of the present invention.

Although the foregoing invention has been described in some detail by way of illustration and example, it should be understood that the invention is not limited thereto, and that many obvious modifications and variations thereof can be made, and that such modifications are intended to fall within the scope of the appended claims.

I claim:

1. A method for removing leucocytes and other deleterious matter from leucocyte-containing blood comprising:
   directing the blood through a leukocyte depletion filter assembly comprising a housing, a porous degassing element, a vent, and a hollow, cylindrical filter element;
   passing the blood through the porous degassing element disposed within the housing;
   venting gas from the housing through the vent in communication with the degassing element, wherein the vent includes a liquophobic membrane which allows the gas but not the blood to flow through the vent; and
   passing the blood through the hollow, cylindrical filter element positioned within the housing, the filter element comprising a depth filter including a fibrous mass of synthetic polymeric fibers capable of decreasing the leucocyte content of the blood at a flow rate capacity of about one to about six liters per minute at a differential pressure of less than 15 psi, said fibrous mass having a CWST of at least 53 dynes/cm.

2. The method of claim 1 wherein the blood comprises blood to be processed in an extracorporeal circuit, the method further comprising repeatedly removing blood from a patient, removing leukocytes from the blood, and returning the leukocyte-depleted blood to the patient.

3. The method of claim 2 comprising processing blood in an extracorporeal circuit for greater than 3 hours without clogging the filter element.

4. The method of claim 2 including repeatedly processing blood in an extracorporeal circuit by passing the blood through a leukocyte depletion filter assembly having the capacity to filter the blood for up to about 10 hours without clogging.

5. The method of claim 2 comprising passing the blood through the filter element at a flow rate of about three liters per minute.

6. The method of claim 2 comprising passing the blood through the filter element having a capacity to pass blood at a flow rate of about six liters per minute.

7. The method of claim 1 wherein passing the leukocyte-containing blood through the hollow, cylindrical filter element comprises passing the blood through a corrugated cylindrical filter element.

8. The method of claim 1 wherein passing the blood through a filter element comprises passing blood through an element having a total fiber surface area greater than about two square meters.

9. The method of claim 8 comprising passing the blood through the filter element at a flow rate of about four to about six liters per minute.

10. The method of claim 1 wherein passing the blood through the hollow cylindrical filter element comprises passing the blood through a corrugated cylinder having an outer diameter in the range of about 2 to about 3 inches.

11. A method for removing leukocytes and other deleterious matter from blood comprising:
    passing the blood through a hollow, cylindrical depth filter including a fibrous filter element having a fibrous surface area of greater than about 2 square meters and a CWST of at least about 53 dynes/cm;
    at a flow rate of about one to about six liters per minute at a differential pressure of less than 15 psi; and
    removing a clinically or therapeutically significant amount of leukocytes from the blood.

12. The method of claim 11 further comprising passing blood repeatedly through the fibrous filter element in an extracorporeal circuit.

13. The method of claim 12 comprising processing blood in an extracorporeal circuit including passing the blood through a fibrous filter element having the capacity to remove leukocytes at a flow rate of greater than about 3 liters per minute for greater than 3 hours without clogging the filter element.

14. The method of claim 11 including separating gas from the blood and venting the gas.

15. The method of claim 1 wherein passing the blood through the hollow, cylindrical fibrous depth filter comprises passing the blood through a corrugated depth filter.

16. A leucocyte depletion filter assembly for removing leucocytes and other deleterious matter from leucocyte-containing blood, the filter assembly comprising:
    a housing having an inlet which allows inflow into the housing, an outlet which allows outflow from the housing, and a vent;
    porous degassing element positioned within the housing to remove gas from the blood;
    a liquophobic membrane covering the vent and communicating with the degassing element to allow gas but not the blood to flow through the vent; and
    a hollow, cylindrical filter element positioned within the housing between the inlet and the outlet and comprising a depth filter including a fibrous mass of synthetic, polymeric fibers capable of decreasing the leucocyte content of the blood at a flow rate capacity of about one to about six liters per minute at a differential pressure of less than 15 psi, said fibrous mass having a CWST of at least 53 dynes/cm.

17. The filter assembly of claim 16 having the capacity to decrease the leukocyte content of the blood at a flow rate of about four to about six liters per minute.

18. The filter assembly of claim 16 having the capacity to decrease the leukocyte content of the blood at a flow rate of about three liters per minute.

19. The filter assembly of claim 18 wherein the hollow, cylindrical filter element comprises a corrugated depth filter.

20. The filter assembly of claim 16 wherein the hollow, cylindrical filter element comprises a corrugated cylindrical element.

21. The filter assembly of claim 16 wherein the filter element includes a voids volume in the range of about 60 to about 95%.

22. The filter assembly of claim 21 wherein the voids volumes is in the range of about 75 to about 85%.

23. The filter assembly of claim 16 wherein the filter element comprises polybutylene terephthalate fibers or polyethylene terephthalate fibers.

24. The filter assembly of claim 16 wherein said filter element has a total fibrous surface area of greater than about two square meters.

25. The filter assembly of claim 16 wherein the housing includes first and second chambers, said degassing element positioned between the first and second chambers, and said filter element positioned in the second chamber.

26. The filter assembly of claim 16 wherein said housing is generally cylindrical, said inlet allows tangential inflow into the first chamber, and said outlet allows outflow from the second chamber.

27. The filter assembly of claim 16 wherein the filter element includes an outer diameter in the range of about 2 to about 3 inches.

28. The filter assembly of claim 16 including a hold up volume in the range of from about 70 cc to about 400 cc.

29. A leukocyte depletion filter assembly for removing leukocytes and other deleterious matter from leukocyte-containing blood, the filter assembly comprising:

a housing having an inlet and an outlet and defining a blood flow path between the inlet and the outlet, and a hollow, cylindrical fibrous depth filter positioned across the blood flow path and including a microfibrous mass for decreasing the leukocyte content of the blood, said fibrous filter having a CWST of at least 53 dynes/cm and the capacity to decrease the leukocyte content of the blood at a flow rate of about one to about six liters per minute at a differential pressure of less than 15 psi, said hollow, cylindrical fibrous depth filter having a total fiber surface area of greater than about two square meters.

30. The filter assembly of claim 29 including a hold up volume in the range of from about 18 cc to about 250 cc.

31. The filter assembly of claim 29 wherein the hollow, cylindrical fibrous depth filter comprises a corrugated cylinder.

32. A leukocyte depletion filter assembly for removing leukocytes and other deleterious matter from leukocyte-containing blood, the filter assembly comprising:

a housing having an inlet and an outlet and defining a blood flow path between the inlet and the outlet, and a vent;

a fibrous depth filter positioned across the blood flow path and including a microfibrous mass for decreasing the leukocyte content of the blood, said fibrous depth filter comprising a hollow, cylindrical, corrugated filter, and having a CWST of at least 53 dynes/cm and the capacity to decrease the leukocyte content of the blood at a flow rate of about one to about 6 liters per minute at a differential pressure of less than 15 psi, said fibrous depth filter having a total fiber surface area of greater than about two square meters.

33. The assembly of claim 32 including a porous degassing element positioned within the housing to remove gas from the blood.

34. The assembly of claim 33 including a liquophobic membrane covering the vent and communicating with the degassing element to allow gas but not blood to flow through the vent.

35. The filter assembly of claim 32 wherein the hollow, cylindrical fibrous depth filter comprising a corrugated cylinder.

* * * * *